United States Patent
Borschel et al.

(10) Patent No.: US 6,365,218 B1
(45) Date of Patent: Apr. 2, 2002

(54) PEDIATRIC FORMULA AND METHODS FOR PROVIDING NUTRITION AND IMPROVING TOLERANCE

(75) Inventors: Marlene W. Borschel, Worthington; Steven T. Luebbers, Columbus; Cynthia J. Black, Westerville, all of OH (US); Daniel L. McKamy, Simpsonville, SC (US); Timothy Costigan, Upper Arlington, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/498,350

(22) Filed: Feb. 4, 2000

(51) Int. Cl.$^7$ .............................. A23L 1/054; A23L 1/29
(52) U.S. Cl. ......................... 426/573; 426/72; 426/74; 426/801
(58) Field of Search ............................ 426/72, 74, 573, 426/801

(56) References Cited

U.S. PATENT DOCUMENTS

| | | | |
|---|---|---|---|
| 4,282,262 A | | 8/1981 | Blake |
| 4,670,268 A | | 6/1987 | Mahmoud |
| 5,171,602 A | | 12/1992 | Martin et al. |
| 5,192,577 A | | 3/1993 | Masson |
| 5,256,436 A | | 10/1993 | Malone et al. |
| 5,376,396 A | | 12/1994 | Clark |
| 5,429,837 A | * | 7/1995 | Balabaud et al. ............ 426/573 |
| 5,472,952 A | | 12/1995 | Smidt |
| 5,597,595 A | | 1/1997 | DeWille |
| 5,609,897 A | | 3/1997 | Chandler et al. |
| 5,681,600 A | | 10/1997 | Antinone et al. |
| 5,817,351 A | | 10/1998 | DeWille |
| 5,827,544 A | * | 10/1998 | Abu Seir et al. ............ 424/677 |
| 5,858,449 A | | 1/1999 | Crank et al. |
| 5,919,512 A | | 7/1999 | Montezines |
| 6,099,871 A | * | 8/2000 | Martinez ........................ 426/2 |

FOREIGN PATENT DOCUMENTS

| | | |
|---|---|---|
| EP | 0 045 158 A1 | 8/1982 |
| JP | B-252080 | 10/1996 |

OTHER PUBLICATIONS

The dietaty effects of xanthan gum in Man; Food Additives and Contaminants, 1987, vol. 4, No. 1, 17–26.

Physiological Effects of Food Carbohydrates, American Chemical Society, ACS Symposiums Series 15, 269–281.

The effect of feeding xanthan gum on colonic funcytion in man: correlation with in vitro determinants of bacterial breakdown, British Journal of Nutrition (1993), 69, 897–902.

Derwent Abstract WPI Acc No: 96–46411/199649.

Derwent Abstract 96–492332/199649.

Derwent Abstract 82–10272E/198206.

Abstract of Journal of Dairy Science; 78 (11) 2541–2562, 128 ref.

Abstract of EP 0 628 256 A1.

Abstract of Food Engineering; 63 (2) 99–101.

Abstract of US 5,434,078.

Abstract of Trends in Food Science an Technology; 1997. (Dec. ), 8 (12), 395–400 (30 ref.).

* cited by examiner

Primary Examiner—Helen Pratt
(74) Attorney, Agent, or Firm—J. Michael Dixon

(57) ABSTRACT

The present invention provides an improved pediatric formula and methods for providing nutrition to and enhancing tolerance in pediatric patients. The formula may be provided in powder, concentrate or ready-to-feed forms. The pediatric formula comprises, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising about 37 to about 370 milligrams (preferably about 74 to about 222 milligrams, more preferably about 111 to about 148 milligrams) xanthan gum. The formula may also be provided in a powder, which comprises, based on 100 grams of powder, about 30 to about 90 grams carbohydrate (preferably about 48 to about 59), about 15 to about 30 grams lipid (preferably 22 to about 28 grams), about 8 to about 17 grams protein (preferably about 11 to about 17), and about 188 to about 1880 milligrams (preferably about 375 to about 1125, more preferably about 375 to about 1125 milligrams) xanthan gum. The formula preferably further comprises vitamins and minerals and may further comprise a stabilizer. The methods comprise administering to a pediatric patient an effective amount of a pediatric formula according to the invention, as described above.

78 Claims, No Drawings

PEDIATRIC FORMULA AND METHODS FOR PROVIDING NUTRITION AND IMPROVING TOLERANCE

FIELD OF THE INVENTION

The invention relates to a pediatric formula, and particularly relates to enhancing the tolerance of pediatric patients fed the formula. Pediatric patients include both infants (children 12 months of age or less) and children (children more than 12 months of age but less than 13 yrs of age). (Therefore, all infants are children, but not all children will be infants.) More specifically, the invention is a pediatric formula comprising xanthan gum that has been found effective in increasing tolerance in patients fed such a formula. The invention is also a method of providing nutrition and a method of improving tolerance comprising administering an effective amount of a pediatric formula comprising xanthan gum.

BACKGROUND OF THE INVENTION

Pediatric formulas may be classified into three general types based on the type of protein: intact protein-based, hydrolyzed protein-based, and free amino acid-based. (Pediatric formulas encompass infant formulas and formulas intended for children one year and older.) Commercial pediatric formulas may also contain, in addition to a protein source, carbohydrates, lipids, vitamins and minerals. Free amino acids are currently utilized as the pediatric source in pediatric formulas (EleCare™, Ross Products Division of Abbott Laboratories) intended for children one year and older who have one or more of the following: problems digesting and absorbing regular foods, severe food allergies, gastrointestinal tract problems, or other conditions in which an elemental diet is needed.

Many pediatric patients experience intolerance to certain formulas (formula intolerance). The terms intolerance and formula intolerance are used interchangeably herein. Intolerance is a non-immune system associated reaction and may be evidenced by behavior or stool or feeding pattern changes such as increased spit-up or vomiting, an increased number of stools, more watery stools, and increased fussiness as compared to normal infants who tolerate formula well. Intolerance is most often indicated by gastrointestinal symptoms (e.g. emesis, stool patterns and gas) as well as behavioral characteristics (e.g. acceptance of formula, fussing and crying). In clinical study settings such behavior may be cause for parents to remove their infants from a particular study. Infants removed from a study because of such behaviors are referred to as exits for intolerance. In a non-clinical setting such behavior often causes parents to switch formulas.

Intolerance can be contrasted with the allergic-type reactions some infants exhibit to certain formulas. These allergic-type reactions are immune system associated, and may be caused by the infant's sensitivity to the protein present in the formula. Many infants who exhibit allergies or sensitivities to intact (whole) proteins, such as those in intact cow's milk protein or intact soy protein isolate-based formulas, are able to tolerate extensively hydrolyzed protein. (Hydrolysate formulas (also referred to as semi-elemental formulas) contain protein that has been hydrolyzed or broken down into short peptide fragments and amino acids and as a result is more easily digested by all infants.) These immune system associated allergies or sensitivities often result in cutaneous, respiratory or gastrointestinal symptoms such as vomiting and diarrhea. Infants who exhibit reactions to intact protein formulas often will not react to hydrolysate formulas because their immune system does not recognize the hydrolyzed protein as the intact protein that causes their symptoms. Infants who exhibit immune system associated reactions to formulas may also exhibit non-immune system associated reactions (formula intolerance), as previously described.

Many different pediatric formulas are in existence. Much of the previous focus in the art has been on the physical stability of the formulas, and concurrent processing or manufacturing concerns.

U.S. Pat. No. 5,192,577 to Masson discloses and teaches the use of xanthan gum in a nutritional formula but only as a stabilizer and specifically limits that use to formulas that use kappa carrageenan in combination with the xanthan gum. Masson deals primarily with the physical stability of the nutritional formula disclosed therein and does not address the problem of intolerance exhibited by patients fed the formula.

U.S. Pat. No. 5,472,952 to Smidt et al. relates to nutritionally complete food compositions which contain partially hydrolyzed pectin for the management of diarrhea. The use of xanthan gum as an emulsifier or stabilizer is disclosed but no teaching of the amount of xanthan gum is provided.

U.S. Pat. No. 5,681,600 to Anfinone et al. discloses use of xanthan gum in a nutritional formula but teaches that such use of xanthan gum is unacceptable because of unacceptable calcium delivery resulting from use of formulas comprising xanthan gum.

U.S. Pat. No. 4,670,268 to Mahmoud discloses an enteral nutritional hypoallergenic nutritional formula which may contain xanthan gum as a stabilizer but fails to provide any teaching of effective amounts of xanthan gum for that purpose.

U.S. Pat. No. 5,919,512 to Montezinos discloses the use of xanthan gum as a stabilizer in a flavoricloud emulsion such as is present in dilute juice and tea beverages. The emulsion disclosed therein contains no protein and thus, would be unsatisfactory for use as a pediatric formula.

U.S. Pat. No. 5,597,595 to DeWille et al. discloses the use of xanthan gum as an emulsion stabilizer in a low pH beverage fortified with calcium and vitamin D.

U.S. Pat. No. 5,817,351 to DeWille et al. discloses the use of xanthan gum as a stabilizer in low pH beverages that are calcium fortified. The beverages disclosed therein contain no fat and protein and would be unsuitable as a complete nutritional source.

U.S. Pat. No. 5,609,897 to Chandler et al. discloses the use of xanthan gum in a soft drink like powdered beverage that has been fortified with calcium and vitamin D.

U.S. Pat. No. 5,858,449 to Crank et al. discloses the use of xanthan gum in an isoflavone-enriched soy-based frozen dessert.

In general, the prior art nutritional formulas completely fail to address the problem of intolerance. Thus, there is an unmet need for a formula that is more readily tolerated by pediatric patients who exhibit symptoms of intolerance. A formula that is better tolerated will result in behavior more similar to that displayed by normal pediatric patients who tolerate formula well.

SUMMARY OF THE INVENTION

The present invention provides an improved pediatric formula and methods for providing nutrition and increasing the tolerance of children fed the formula. (As used herein, unless otherwise indicated, the term children is meant to encompass both infants and children over one year in age. The terms child/children and pediatric patient are also used interchangeably.) The use of xanthan gum has provided unexpected improvements in tolerance. The formula may be in liquid concentrate, ready-to-feed or powdered form. The formula comprises, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising about 37 to about 370 milligrams (preferably about 74 to about 222 milligrams, more preferably about 111 to about 148 milligrams) xanthan gum. If the formula is provided in a powder form, it comprises based on 100 grams of powder, about 30 to about 90 grams carbohydrate (preferably about 48 to about 59 grams), about 15 to about 30 grams lipid (preferably about 20 to about 30), about 8 to about 17 grams protein (preferably about 10 to about 17 grams), and about 188 to about 1880 milligrams (preferably about 375 to about 1125 milligrams, more preferably about 565 to about 750 milligrams) xanthan gum.

The formula may further comprise a stabilizer and also preferably comprises vitamins and minerals in amounts sufficient to supply the daily nutritional requirements of infants or children over one. When the formula is an infant formula, the amounts of vitamins and minerals are preferably selected according to FDA guidelines. When infants are fed a formula according to the invention, improved tolerance is exhibited by those infants, as compared to infants fed a formula with the same composition but lacking the tolerance improver.

The invention also provides methods of providing nutrition to and improving tolerance in a pediatric patient. The methods comprise feeding the child an effective amount of a formula comprising, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising about 37 to about 370 milligrams (preferably about 74 to about 222 milligrams, more preferably about 111 to about 148 milligrams) xanthan gum. If the formula is provided in a powder form, it comprises based on 100 grams of powder, about 30 to about 90 grams carbohydrate (preferably about 48 to about 59 grams ), about 15 to about 30 grams lipid (preferably about 22 to about 28), about 8 to about 17 grams protein (preferably about 11 to about 17 grams), and about 188 to about 1880 milligrams (preferably about 375 to about 1125 milligrams, more preferably about 565 to about 750 milligrams) xanthan gum. Children fed formulas of the invention exhibit fewer symptoms of intolerance than children fed the same formula but lacking the xanthan gum tolerance improver.

DETAILED DESCRIPTION OF THE INVENTION

The present invention provides an improved pediatric formula that reduces the intolerance of children fed the formula. The invention also provides methods for providing nutrition to and improving tolerance in pediatric patients comprising feeding a formula of the invention. The use of xanthan gum has provided unexpected improvements in tolerance.

Intolerance (formula intolerance) in infants is often indicated by gastrointestinal symptoms (e.g. emesis, stool patterns, and gas) as well as behavioral characteristics (e.g. acceptance of formula, fussing, and crying). For purposes of this invention, improved tolerance (or reduced intolerance) is defined as an improvement (change towards normal patterns) of one or more of the following symptoms or characteristics: stool pattern, vomiting, spit up, acceptance of formula, fussing, crying, or exits for intolerance (clinical setting).

The pediatric formula of the invention may be provided in powdered, liquid concentrate or ready-to-feed forms. Before feeding, water is added to both the powdered and concentrate forms of the formula. In a first embodiment, a pediatric formula of the invention comprises, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising about 37 to about 370 milligrams (preferably about 74 to about 222 milligrams, more preferably about 111 to about 148 milligrams) xanthan gum. If provided in a powder form, the formula comprises, based on 100 grams of powder, about 30 to about 90 grams carbohydrate (preferably about 48 to about 59 grams ), about 15 to about 30 grams lipid (preferably about 22 to about 28), about 8 to about 17 grams protein (preferably about 11 to about 17 grams), and about 188 to about 1880 milligrams (preferably about 375 to about 1125 milligrams, more preferably about 565 to about 750 milligrams) xanthan gum. A summary of the carbohydrate, lipid and protein ranges (on a per 100 kcal basis, per 100 grams powder basis and per liter basis (as fed concentration) for a formula according to the invention is provided in Table I.

Xanthan gum is a high molecular weight polysaccharide produced by fermentation of a carbohydrate by *Xanthomonas campestris*. While xanthan gum is available in various mesh sizes, the use of xanthan gum in this invention is not limited to any particular mesh size. An appropriate mesh size may be selected based on processing parameters, e.q., a finer mesh size (200 mesh) may be preferred if the xanthan gum is to be dry blended into a formula whereas, a more coarse size (80 mesh) may be preferred if the xanthan gum is not dry blended into a formula. A suitable xanthan gum for use in this invention is Keltrol_F Xanthan Gum (200 mesh) available from Kelco, a division of Monsanto, Chicago, Ill.

Suitable carbohydrates, lipids and proteins can vary widely and are well known to those skilled in the art of making pediatric formulas. Suitable carbohydrates may thus include, but are not limited to, hydrolyzed, intact, naturally and/or chemically modified starches sourced from corn, tapioca, rice or potato in waxy or non waxy forms; and sugars such as glucose, fructose, lactose, sucrose, maltose, high fructose corn syrup, and mixtures thereof. Maltodextrins are polysaccharides obtained from the acid or enzyme hydrolysis of starches such as those from corn or rice. Their classification is based on the degree of hydrolysis and is reported as dextrose equivalent (DE). When protein hydrolysates are the protein source, the DE of any maltodextrin utilized is preferably less than about 18–20. When protein hydrolysates are the protein source it is also preferable to avoid conditions which could lead to the formation of excessive Maillard browning products.

Suitable lipids include, but are not limited to, coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof. Lipid sources of arachidonic acid and docosahexaneoic acid include, but are not limited to, marine oil, egg yolk oil, and fungal oil.

Suitable protein sources include milk, soy, rice, meat (e.g., beef), animal and vegetable (e.g., pea, potato), egg (egg albumen), gelatin, and fish. Suitable intact proteins include, but are not limited to, soy based, milk based, casein protein, whey protein, rice protein, beef collagen, pea protein, potato protein and mixtures thereof. Suitable protein hydrolysates also include, but are not limited to, soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof. Hydrolyzed proteins (protein hydrolysates) are proteins that have been hydrolyzed or broken down into shorter peptide fragments and amino acids. Such hydrolyzed peptide fragments and free amino acids are more easily digested. In the broadest sense, a protein has been hydrolyzed when one or more amide bonds have been broken. Breaking of amide bonds may occur unintentionally or incidentally during manufacture, for example due to heating or shear. For purposes of this invention, the term hydrolyzed protein means a protein which has been processed or treated in a manner intended to break amide bonds. Intentional hydrolysis may be effected, for example, by treating an intact protein with enzymes or acids. The hydrolyzed proteins that are preferably utilized in formulas according to this invention are hydrolyzed to such an extent that the ratio of the amino nitrogen (AN) to total nitrogen (TN) ranges from about 0.1 AN to 1.0 TN to about 0.4 AN to about 1.0 TN, preferably about 0.25 AN to 1.0 TN to about 0.4 AN to about 1.0 TN. (AN:TN ratios given are for the hydrolysate protein source alone, and do not represent the AN:TN ratio in the final pediatric nutritional formula product, since free amino acids may be added as a supplement and would alter the reported value.) Protein may also be provided in the form of free amino acids. A formula according to the invention is preferably supplemented with various free amino acids in order to provide a more nutritionally complete and balanced formula. Examples of suitable free amino acids include, but are not limited to, tryptophan, tyrosine, cystine, taurine, L-methionine, L-arginine, and carnitine.

A formula of the invention preferably also contains vitamins and minerals in an amount designed to supply the daily nutritional requirements of a pediatric patient. The formula preferably includes, but is not limited to, the following vitamins and minerals: calcium, phosphorus, sodium, chloride, magnesium, manganese, iron, copper, zinc, selenium, iodine, and Vitamins A, E, C, D, K and the B complex. Further nutritional guidelines for infant formulas can be found in the Infant Formula Act, 21 U.S.C. section 350(a). The nutritional guidelines found in the Infant Formula Act continue to be refined as further research concerning infant nutritional requirements is completed. This invention is intended to encompass formulas containing vitamins and minerals that may not currently be listed in the Act.

In a second embodiment of the invention, the invention formula further comprises a stabilizer. Suitable stabilizers for use in pediatric nutritional formulas are well known to those skilled in the art. Suitable stabilizers include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof. A formula according to the invention preferably is free of kappa carrageenan as a stabilizer, and most preferably is free of a carrageenan. A formula is defined as being free of kappa carrageenan if any carrageenan utilized is predominately in another form (iota or lambda). For purposes of this invention, free of kappa carrageenan or free of carrageenan means that no kappa carrageenan or carrageenan is added during manufacturing. The amount of stabilizers utilized will vary depending upon the stabilizer(s) selected, the other ingredients present, and the stability and viscosity of the formula that is sought. Appropriate amounts can be determined by those of skill in the art based on the particular characteristics (e.g., viscosity) being sought in the formula.

The invention also provides methods of providing nutrition to and improving tolerance in a pediatric patient. The methods comprise feeding the child an effective amount of a formula comprising, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising about 37 to about 370 milligrams (preferably about 74 to about 222 milligrams, more preferably about 111 to about 148 milligrams) xanthan gum. If the formula is provided in a powder form, it comprises based on 100 grams of powder, about 30 to about 90 grams carbohydrate (preferably about 48 to about 59 grams ), about 15 to about 30 grams fat (preferably about 22 to about 28), about 8 to about 17 grams protein (preferably about 11 to about 17 grams), and about 188 to about 1880 milligrams (preferably about 375 to about 1125 milligrams, more preferably about 565 to about 750 milligrams) xanthan gum.

In another embodiment, the formula may further comprise a stabilizer. Either embodiment also preferably comprises vitamins and minerals, in amounts as discussed above. Suitable carbohydrates, lipids, proteins or proteins, and stabilizers are well known to those skilled in the art and may include, but are not limited to, the substances described above. Preferably, if the formula is an infant formula, the method comprises feeding a sufficient amount of the formula to fulfill all of the infant's daily nutritional requirements.

The pediatric formulas of this invention can be manufactured using techniques well known to those skilled in the art. Various processing techniques exist for producing powdered, ready-to-feed and concentrate liquid formulas. Typically, these techniques include formation of a slurry from one or more solutions which may contain water and one or more of the following: carbohydrates, proteins, lipids, stabilizers, vitamins and minerals. This slurry is emulsified, homogenized and cooled. Various other solutions may be added to the slurry before processing, after processing or at both times. The processed formula is then sterilized and may be diluted to be utilized on a ready-to-feed basis or stored in a concentrated liquid or a powder. If the resulting formula is meant to be a ready-to-feed liquid or concentrated liquid, an appropriate amount of water would be added before sterilization. If the resulting formula is meant to be a powder, the slurry will be heated and dried to obtain a powder. The powder resulting from drying may be dry blended with further ingredients, if desired.

The following examples are illustrative of the methods and compositions of the invention for improving tolerance in pediatric patients. While the invention is described in terms of a powdered infant nutritional formula in the examples, below, it is not intended to be so limited, as it is intended to encompass both ready-to-feed and concentrate liquid infant formulas as well as formulas for children one year in age or older. The examples are not intended to be limiting as other carbohydrates, lipids, proteins, stabilizers, vitamins and minerals may be used without departing from the scope of the invention.

EXAMPLE 1

Clinical Study

Following is a summary of the results of a clinical study on tolerance where infants were fed one of four different formulas. Three different formulas of the invention and a control formula (identical but lacking the xanthan gum tolerance improver) were utilized. The masked, randomized, parallel tolerance study was conducted on healthy, term infants, 28 days or less in age. The infants were fed commercially-labeled Alimentum Protein Hydrolysate Formula With Iron (Ross Products Division, Abbott Laboratories) in a ready-to-feed composition, for one week as a baseline. Immediately thereafter, they randomly received either a control formula or one of formulas B, C or D. The composition of the control formula was identical to that of formulas B–D, except for the presence of differing amounts of xanthan gum in the formulas B–D. The composition of all four formulas is provided in Tables II and II A. The control and formulas B–D were provided in powdered form in metal cans of sufficient size to contain 350 grams when reconstituted with water.

Infants were eligible for the study if they were judged to be in good health; were full-term with a gestational age of 37 to 42 weeks; had a birth weight greater than 2500 g; were at least 28 days of age; were exclusively formula fed at the time of the study; had parents who voluntarily signed an informed consent form; had parents who agreed not to admirnister mineral or vitamin supplements; had parents who agreed to feed their infant only the study formula for the duration of the study; were the product of a single birth pregnancy; did not have a maternal medical history which may have adversely affected the fetus such as diabetes, tuberculosis, perinatal infections, or substance abuse; did not show evidence of cardiac, respiratory, gastrointestinal, hematological, or metabolic disease; and did not have a birth weight greater than the 95th percentile (NCHS (National Center for Health Statistics)) for infants whose mothers had gestational diabetes.

Infants were identified by the investigators from the local population, and eligible infants were recruited. A total of 182 infants, from three different sites, were enrolled in the study. Of the initial 182, 45 exited during the baseline period and never received the control or formulas B–D. Of the 137 who received either the control or one of the formulas B–D, 12 infants failed to complete the study.

Day one of the study was defined as the day of enrollment into the study. On day one, demographictentrance data was collected and infants were weighed unclothed. Parents received approximately twelve 32-fl oz cans of the baseline Alimentum Protein Hydrolysate Formula With Iron in a ready to feed composition. Parents were instructed to continue feeding their current formula until 6:00 p.m. on day one, and then to begin feeding the baseline formula on the first feed after 6:00 p.m on day one. Intake and stool data were collected beginning on day one at 6:00 p.m. and ending at 5:59 p.m. on day seven. Parents also recorded the characteristics of their infants stools, volume of formula consumed at each feeding and incidence of spit up and vomiting.

On day eight of the study, records completed by parents were reviewed by study personnel for completeness and accuracy, infants were reweighed and questionnaires regarding formula satisfaction and feeding and stool patterns were completed by the parents. Parents returned unused baseline formula and were given approximately four cans of one of the assigned formulas the control, B, C or D. Parents were instructed to continue feeding the baseline formula until 6:00 p.m. on day eight, and to begin feeding the assigned formula thereafter and record feeding and stool information. Intake and stool data were collected from day eight starting at 6:00 p.m. and ending at 5:59 p.m. on study day fourteen. Six days of data were collected on the control and formulas B–D. As with the baseline feedings, the dietary intake and stool records completed by parents during days eight to fourteen were reviewed by study personnel at a visit on day fifteen. On day fifteen, infants were weighed, questionnaires were completed and parents returned any unused portions of the formulas.

Statistical Analysis

Primary variables were average daily stool number, mean rank stool consistency and incidence of vomiting and spit up. The primary analysis consisted of an analysis of the primary outcome variables on an intent-to-treat basis. The secondary analysis was conducted with study completers. The study period data were analyzed using one-way analysis of variance with site as blocking factor. Additionally, an analysis of covariance with study period data as response, and baseline data as covariate was done as a confirmatory analysis. Transformations (ranking arcsine of the square root) were applied when appropriate. Categoricalordinal data were analyzed using contingency table methods. All tests were two-sided and performed at the 0.05 significance level. The significance level in the three primary analysis was adjusted for multiplicity of testing using Holm's step-down Bonferroni method.

Results

No statistically significant differences were observed in ethnicity or age on study day one. Significant differences were observed in gender distribution among groups at entry. ($P<0.05$). Weight at day one was significantly greater in the group fed formula B, compared to the group fed the control formula on day one. Significantly more infants fed the control formula exited due to intolerance than compared to those receiving formulas B, C or D (those containing the xanthan gum tolerance improver).

Statistically significant differences were observed among groups in the average daily number of stools ($P=0.003$ adjusted for multiplicity). Infants fed the control formula passed significantly more stools than compared to infants fed formulas B ($P=0.0001$) and D ($P=0.0073$). Infants fed the control formula passed a mean of $2.7\pm0.2$ stools per day and infants fed formula B and D passed a mean of $1.6\pm0.2$ and $2.1\pm0.3$ stools per day during the experimental period (days 8–14). There were no statistically significant differences among groups in mean rank stool consistency. The percent of stools which were watery were significantly different among groups. Infants fed the control formula had significantly more stools which were watery compared to the formula C and D groups ($P<0.01$) when baseline measurements were added as covariate in the analysis. No other significant differences were observed among groups for other stool parameters (loose/mushy, soft, formed). Results on daily number of stools, mean rank stool consistency, watery, loose/mushy stools, soft stools and formed stools are reported in Table III.

No statistically significant differences were observed among groups in the percent of feedings with spit up or the percent of feedings with vomiting. No statistically significant differences were observed in the number of feedings per day, intakes in ml per day, or intakes in ml per kg per day among groups. Results on spit ups, vomiting, feedings per day, intakes in ml per day and intakes in ml per kg per day are reported in Table IV.

No significant differences were observed among groups in weight NCHS Z-scores at day fifteen, or weight gain during the experimental period (days 8–14). A significant difference was observed among groups in weight of infants at the day 15 visit. Infants fed formula B were significantly heavier than infants fed the control formula (P<0.01) as they had been at day one. When day eight weight was used as a covariate, no significant differences were observed among groups in the weight at the end of the study. Results are reported in Table V.

Discussion

The results of the study confirmed that the addition of xanthan gum to a formula improved the tolerance of infants fed such a formula. Infants fed formulas B, C and D (with xanthan gum tolerance improver) generally passed fewer stools per day than those fed the control formula (Table II). Corroborative results found that infants fed formulas B, C and D were judged by parents to have fewer days with too many stools compared to those fed the control formula. In addition, the number of infants exiting due to formula intolerance was significantly lower in the groups fed formulas B, C and D compared to the group fed the control formula. Results are shown in Table VI. The percentage of exits for the group fed the control formula, with no tolerance improver, was 22%. Thus, the reduction in exits (0–6%) for infants fed formulas B, C and D were clinically striking compared to the control. While the infants enrolled in this study were healthy infants (with no known allergy or sensitivity to intact proteins), the improved tolerance results achieved here should also be experienced by infants with allergies or sensitivities to intact proteins who exhibit symptoms of intolerance while on current hydrolysate formulas and by children over one who exhibit symptoms of intolerance.

EXAMPLE 2

A powdered formula is prepared by solubilizing approximately 6870 lb. corn maltodextrin, 3095 lb. sucrose, 24.4 kg magnesium chloride, 54.9 kg potassium citrate, 17.8 kg sodium chloride, 114.5 kg calcium phosphate, tribasic, 25.5 kg calcium carbonate, 16.4 kg potassium chloride and 13.7 g potassium iodide in water at 160° F. to make an aqueous solution. The amount of water used in making the aqueous solution will be optimized for the particular manufacturing equipment utilized. This solution is blended with a second solution containing 1911 lb. MCT oil, 130.6 kg diacetyl tartaric acid esters of mono- and diglycerides, 26.1 kg mono- and diglycerides, 2020 lb. high oleic safflower oil, 1.1 lb. mixed tocopherols, 1613 lb. soy oil, 2.1 kg ascorbyl palmitate and 3.2 kg of a vitamin premix containing vitamin A palmitate, vitamin E acetate, phylloquinone and vitamin D3 to form a slurry. This slurry is mixed for a minimum of 30 minutes up to two hours at a temperature of 68 to 74° C. This slurry is emulsified at 1000 psi, homogenized through a two-stage homogenizer at 2500 psi/500 psi and cooled through a plate heat exchanger to approximately 4° C. Solutions containing free amino acids, water soluble vitamins and trace minerals are added to the processed slurry. The slurry is heated to 74.4 to 85° C. for a minimum of 16 seconds and spray dried to obtain a powder having a moisture content of approximately 1.5%. The spray dried powder is dry blended with approximately 3430 lb. casein hydrolysate and 51.2 kg of xanthatn gum.

EXAMPLE 3

A powdered formula is prepared by solubilizing approximately 6870 lb. corn maltodextrin, 3095 lb. sucrose, 24.4 kg magnesium chloride, 54.9 kg potassium citrate, 17.8 kg sodium chloride, 114.5 kg calcium phosphate, tribasic, 25.5 kg calcium carbonate, 16.4 kg potassium chloride and 13.7 g potassium iodide in water at 160° F. to make an aqueous solution. The amount of water used in making the aqueous solution will be optimized for the particular manufacturing equipment utilized. This solution is blended with a second solution containing 1911 lb. MCT oil, 130.6 kg diacetyl tartaric acid esters of mono- and diglycerides, 26.1 kg mono- and diglycerides, 2020 lb. high oleic safflower oil, 1.1 lb. mixed tocopherols, 1613 lb. soy oil, 2.1 kg ascorbyl palmitate and 3.2 kg of a vitamin premix containing vitamin A palmitate, vitamin E acetate, phylloquinone and vitamin D3 to form a slurry. This slurry is mixed for a minimum of 30 minutes up to two hours at a temperature of 68 to 74° C. This slurry is emulsified at 1000 psi, homogenized through a two-stage homogenizer at 2500 psi/500 psi and cooled through a plate heat exchanger to approximately 4° C. Approximately 3430 lb. casein hydrolysate is blended in water for a minimum of 30 minutes up to two hours at a temperature of 68–74° C. This slurry is emulsified at 1000 psi, homogenized through a two-stage homogenizer at 2500 psi/500 psi, cooled through a plate heat exchanger to approximately 4° C. and added to the carbohydrate/fat/lipid blend. Solutions containing free amino acids, water soluble vitamins and trace minerals are added to the processed slurry. The slurry is heated to 74.4 to 85° C. for a minimum of 16 seconds and spray dried to obtain a powder having a moisture content of approximately 1.5%. The spray dried powder is dry blended with 51.2 kg of xanthan gum.

EXAMPLE 4

A powdered formula is prepared by solubilizing approximately 6870 lb. corn maltodextrin, 3095 lb. sucrose, 24.4 kg magnesium chloride, 54.9 kg potassium citrate, 17.8 kg sodium chloride, 114.5 kg calcium phosphate, tribasic, 25.5 kg calcium carbonate, 16.4 kg potassium chloride and 13.7 g potassium iodide in water at 160° F. to make an aqueous solution. The amount of water used in making the aqueous solution will be optimized for the particular manufacturing equipment utilized. This solution is blended with a second solution containing 1911 lb. MCT oil, 130.6 kg diacetyl tartaric acid esters of mono and diglycerides, 26.1 kg mono- and diglycerides, 2020 lb. high oleic safflower oil, 1.1 lb. mixed tocopherols, 1613 lb. soy oil, 2.1 kg ascorbyl palmitate, 3.2 kg of a vitamin premix containing vitamin A palmitate, vitamin E acetate, phylloquinone and vitamin D3 and the xanthan gum to form a slurry. This slurry is mixed for a minimum of 30 minutes up to two hours at a temperature of 68 to 74° C. This slurry is emulsified at 1000 psi, homogenized through a two-stage homogenizer at, 2500 psi/500 psi and cooled through a plate heat exchanger to approximately 4° C. Approximately 3430 lb. casein hydrolysate is blended in water for a minimum of 30 minutes up to two hours at a temperature of 68–74° C. This slurry is emulsified at 1000 psi, homogenized through a two-stage homogenizer at 2500 psi/500 psi, cooled through a plate heat exchanger to approximately 4° C. and added to the carbohydratelfatilipid blend. Solutions containing free amino acids, water soluble vitamins and trace minerals are added to the processed slurry. The slurry is heated to 74.4 to 85° C. for a minimum of 16 seconds and spray dried to obtain a powder having a moisture content of approximately 1.5%.

EXAMPLE 5

A powdered formula is prepared by solubilizing approximately 6870 lb. rice maltodextrin, 3095 lb. sucrose, 24.4 kg magnesium chloride, 54.9 kg potassium citrate, 17.8 kg sodium chloride, 114.5 kg calcium phosphate, tribasic, 25.5 kg calcium carbonate, 16.4 kg potassium chloride and 13.7 g potassium iodide in water at 160° F. to make an aqueous solution. This solution is blended with a second solution containing 1911 lb. MCT oil, 130.6 kg diacetyl tartaric acid esters of mono- and diglycerides, 26.1 kg mono- and diglycerides, 2020 lb. high oleic safflower oil, 1.1 lb. mixed tocopherols, 1613 lb. soy oil, 2.1 kg ascorbyl palmitate and 3.2 kg of a vitamin premix containing vitamin A palmitate, vitamin E acetate, phylloquinone and vitamin D3. to form a slurry. This slurry is mixed for a minimum of 30 minutes up to two hours at a temperature of 68 to 74° C. This slurry is emulsified at 1000 psi, homogenized through a twostage homogenizer at 2500 psi/500 psi and cooled through a plate heat exchanger to approximately 4° C. Solutions containing water soluble vitamins and trace minerals are added to the processed slurry. The slurry is heated to 74.4 to 85° C. for a minimum of 16 seconds and spray dried to obtain a powder having a moisture content of approximately 1.5%. The spray dried powder is dry blended with approximately 3430 lb. whey protein hydrolysate, free amino acids, 41.2 kg locust bean gum and 51.2 kg of xanthan gum.

While the invention has been described herein with reference to particular embodiments, it is to be understood that it is not intended to limit the invention to the specific forms disclosed. On the contrary, it is intended to cover all modifications and alternative forms falling within the spirit and scope of the invention.

TABLE I

RANGES OF CARBOHYDRATE, LIPID AND PROTEIN PER 100 KCAL, PER 100 GRAMS POWDER AND PER LITER (AS FED CONCENTRATION)

| Nutrient (g) | Range | Per 100 kcal | Per 100 grams powder | Per liter (as fed concentration) |
|---|---|---|---|---|
| Carbohydrate | Broadest | 8–16 | 30–90 | 53–107 |
|  | Preferred | 9.4–12.3 | 48–59 | 64–83 |
| Lipid | Broadest | 3–6 | 15–30 | 22–40 |
|  | Preferred | 4.7–5.6 | 22–28 | 32–38 |
| Protein | Broadest | 1.8–3.3 | 8–17 | 12–22 |
|  | Preferred | 2.4–3.3 | 11–17 | 16–22 |

TABLE II

NUTRIENT CONTENT OF CONTROL AND FORMULAS B, C, AND D*

| Nutrient[1] | Per Liter | Per 100 kcal | Per 100 g Powder |
|---|---|---|---|
| Protein (g) | 18.6 | 2.75 | 13.9 |
| Fat (g) | 37.5 | 5.55 | 28.1 |
| Carbohydrate (g) | 73 | 10.8 | 54.6 |
| Calcium (mg) | 710 | 105 | 531 |
| Phosphorus (mg) | 507 | 75 | 379 |
| Magnesium (mg) | 51 | 7.5 | 38.1 |
| Iron (mg) | 12.2 | 1.8 | 9.1 |
| Zinc (mg) | 5 | 0.74 | 3.7 |
| Manganese (mcg) | 34 | 5 | 25 |
| Copper (mcg) | 500 | 74 | 374 |
| Iodine (mcg) | 100 | 14.8 | 75 |
| Sodium (mg) | 297 | 43.9 | 222 |
| Potassium (mg) | 800 | 118.3 | 598 |
| Chloride (mg) | 541 | 80 | 405 |
| Selenium (mcg) | 16 | 2.4 | 12 |
| Vitamin A (IU) | 2,200 | 325 | 1,646 |
| Vitamin D (IU) | 400 | 59 | 299 |
| Vitamin E (IU) | 20.8 | 3.1 | 15.6 |
| Vitamin $K_1$ (IU) | 101 | 14.9 | 75.5 |
| Thiamin (mcg) | 580 | 86 | 434 |
| Riboflavin (mcg) | 600 | 89 | 449 |
| Vitamin B-6 (mcg) | 530 | 78 | 396 |
| Vitamin B-12 (mcg) | 3 | 0.44 | 2.24 |
| Niacin (mg) | 9 | 1.33 | 6.73 |
| Folic Acid (mcg) | 100 | 14.8 | 74.8 |
| Panthothenic Acid (mg) | 5 | 0.74 | 3.74 |
| Biotin (mcg) | 30 | 4.4 | 22.4 |
| Vitamin C (mg) | 90 | 13.3 | 67.3 |
| Choline (mg) | 53 | 7.8 | 39.6 |
| Inositol (mg) | 30 | 4.4 | 22.4 |

*Values are minimum except for carbohydrate which is maximum based on minimum protein and fat.

TABLE IIA

AMOUNT OF XANTHAN GUM (MG) IN CONTROL AND FORMULAS B, C, AND D

| Formula | Per Liter | Per 100 kcal | Per 100 g Powder |
|---|---|---|---|
| A | 0 | 0 | 0 |
| B | 500 | 74 | 374 |
| C | 1,000 | 148 | 748 |
| D | 1,500 | 222 | 1,122 |

TABLE III

Number Of Stools Per Day, Mean Rank Stool Consistency, And Percent Of Watery, Loose/Mushy, Soft And Formed Stools During Baseline and Experimental Periods[1]

| Parameter | Group/Formula | Baseline (Days 1–7) | Experimental (Days 1–8) |
|---|---|---|---|
| Stools (number/day) | Control | 2.7 ± 0.2 | 2.7 ± 0.2 |
|  | B | 2.6 ± 0.3 | 1.6 ± 0.2 |
|  | C | 2.6 ± 0.3 | 1.9 ± 0.2 |
|  | D | 2.5 ± 0.3 | 2.1 ± 0.3 |
| Mean Rank Stool Consistency[2] | Control | 2.5 ± 0.1 | 2.1 ± 0.1 |
|  | B | 2.4 ± 0.1 | 2.0 ± 0.1 |
|  | C | 2.3 ± 0.1 | 2.3 ± 0.1 |
|  | D | 2.3 ± 0.1 | 2.3 ± 0.1 |
| % Watery Stools | Control | 6.9 ± 2.3 | 29.0 ± 6.1 |
|  | B | 8.9 ± 2.7 | 22.6 ± 5.4 |
|  | C | 13.2 ± 3.6 | 11.0 ± 4.3 |
|  | D | 11.6 ± 2.7 | 14.2 ± 4.2 |
| % Loose/Mushy Stools | Control | 41.6 ± 5.1 | 42.1 ± 5.5 |
|  | B | 47.7 ± 5.3 | 51.9 ± 6.3 |
|  | C | 49.1 ± 5.4 | 51.3 ± 7.2 |
|  | D | 52.6 ± 4.3 | 42.6 ± 6.2 |
| % Soft Stools | Control | 45.4 ± 5.4 | 22.6 ± 4.9 |
|  | B | 38.0 ± 5.4 | 25.4 ± 6.3 |
|  | C | 31.6 ± 5.0 | 33.8 ± 7.5 |
|  | D | 31.8 ± 4.0 | 37.0 ± 5.8 |
| % Formed Stools | Control | 5.7 ± 1.9 | 6.3 ± 3.2 |
|  | B | 5.3 ± 1.9 | 0.0 ± 0.0 |
|  | C | 5.5 ± 2.7 | 2.2 ± 1.4 |
|  | D | 3.4 ± 1.2 | 5.4 ± 2.3 |

[1]Mean ± standard error of the mean.
[2]1 = watery, 2 = loose/mushy, 3 = soft, 4 = formed, 5 = hard.

TABLE IV

Number Of Feedings Per Day,
Average Intake, and Percent of Feeding With Spit Up, Vomiting And
Spit Up And Vomiting During Baseline And Experimental Periods[1]

| Parameter | Group/Formula | Baseline (Days 1–7) | Experimental (Days 1–8) |
|---|---|---|---|
| Number of feedings/day | Control | 7.5 ± 0.2 | 7.3 ± 0.3 |
| | B | 7.4 ± 0.2 | 7.3 ± 0.3 |
| | C | 7.4 ± 0.3 | 7.1 ± 0.3 |
| | D | 7.2 ± 0.2 | 6.9 ± 0.2 |
| Average Intake (ml/day) | Control | 524 ± 19 | 568 ± 26 |
| | B | 556 ± 28 | 624 ± 32 |
| | C | 525 ± 21 | 605 ± 24 |
| | D | 551 ± 26 | 608 ± 21 |
| % Feedings with Spit Up | Control | 11.1 ± 2.0 | 13.3 ± 3.5 |
| | B | 17.0 ± 3.1 | 11.7 ± 2.1 |
| | C | 23.8 ± 4.3 | 15.0 ± 4.2 |
| | D | 11.5 ± 2.2 | 9.0 ± 1.8 |
| % of Subjects with any Vomiting | Control | 8.2 ± 2.9 | 2.0 ± 1.0 |
| | B | 4.1 ± 1.4 | 3.9 ± 2.9 |
| | C | 7.3 ± 2.6 | 3.6 ± 2.0 |
| | D | 4.8 ± 1.6 | 2.6 ± 1.0 |
| % of Feedings with Spit Up or Vomit | Control | 19.3 ± 3.5 | 15.3 ± 3.5 |
| | B | 21.0 ± 3.8 | 15.6 ± 3.3 |
| | C | 31.2 ± 5.1 | 18.6 ± 4.5 |
| | D | 16.3 ± 3.2 | 11.5 ± 2.3 |

[1]Mean ± standard error of the mean.

TABLE V

Weight Gain Of Infants During The Baseline
And Experimental Periods[1]

| Parameter | Group/Formula | Baseline (Days 1–7) | Experimental (Days 8–14) |
|---|---|---|---|
| Weight Gain (grams/day) | Control[2] | 30.2 ± 2.7 | 31.1 ± 2.9 |
| | B[3] | 33.6 ± 2.6 | 34.4 ± 2.1 |
| | C[4] | 29.3 ± 2.8 | 30.9 ± 2.8 |
| | D[5] | 26.6 ± 2.4 | 34.1 ± 2.7 |

[1]Mean ± standard error of the mean.
[2]Number of infants: 44 baseline, 35 experimental.
[3]Number of infants: 43 baseline, 35 experimental.
[4]Number of infants: 39 baseline, 28 experimental.
[5]Number of infants: 44 baseline, 36 experimental.

TABLE VI

Subject Outcome By Feeding (n = 182)

| | | Formula | | |
|---|---|---|---|---|
| Exit Status | Control | B | C | D |
| Successful Completion | 29 | 33 | 28 | 35 |
| Early Exit (Days 8–14)[1] | 8 | 2 | 0 | 2 |
| Baseline Exit (Days 1–7) | 9 | 11 | 17 | 8 |
| Percentage of Exits[2] | 22 | 6 | 0 | 5 |
| Total | 46 | 46 | 45 | 45 |

[1]All due to formula intolerance or parental dissatisfaction except for one infant in the 1500 group.
[2]Percent = [early exits (days 8–14)/[successful completers ± baseline exits (days 1–7)]] × 100

What is claimed is:

1. A pediatric formula comprising, based on a 100 kcal basis: about 8 to about 16 grams carbohydrate, about 3 to about 6 grams lipid, about 1.8 to about 3.3 grams protein, and a tolerance improver, consisting of a single hydrocolloid which is selected from the group consisting of xanthan gum in the amounts of about 37 to 370 milligrams.

2. A pediatric formula as defined in claim 1 wherein the xanthan gum comprises from about 74 to about 222 milligrams.

3. A pediatric formula as defined in claim 1 wherein the xanthan gum comprises from about 111 to about 148 milligrams.

4. A pediatric formula as defined in claim 1 wherein the carbohydrate comprises from about 9.4 to about 12.3 grams.

5. A pediatric formula as defined in claim 1 wherein the lipid comprises from about 4.7 to about 5.6 grams.

6. A pediatric formula as defined in claim 1 wherein the protein comprises from about 15 2.4 to about 3.3 grams.

7. A pediatric formula as defined in claim 1 further comprising vitamins and minerals.

8. A pediatric formula as defined in claim 1 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

9. A pediatric formula as defined in claim 1 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

10. A pediatric formula as defined in claim 1 wherein the protein comprises intact protein selected from the group consisting of soy based protein, milk based protein, casein protein, whey protein, rice protein, beef collagen, pea protein, potato protein, and mixtures thereof.

11. A pediatric formula as defined in claim 1 wherein the protein comprises hydrolyzed protein selected from the group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

12. A pediatric formula as defined in claim 1 wherein the protein comprises free amino acids selected from the group consisting of tryptophan, tyrosine, cystine, taurine, L-methionine, L-arginine, and carnitine, and mixtures thereof.

13. A pediatric formula as defined in claim 1 wherein the carbohydrate is selected from the group consisting of hydrolyzed, intact, natural and chemically modified starches sourced from corn, tapioca, rice or potato in waxy or non waxy forms; sugars such as glucose, fructose, lactose, sucrose, maltose, high fructose corn syrup; and mixtures thereof.

14. A pediatric formula in a powdered form which comprises, based on 100 grams of powder, about 30 to about 90 grams carbohydrate, about 15 to about 30 grams lipid, about 8 to about 17 grams protein, and a tolerance improver consisting of a single hydrocolloid which is selected from the group consisting of xanthan gum in amounts of about 188 to about 1880 milligrams.

15. A pediatric formula as defined in claim 14 wherein the xanthan gum comprises from about 375 to about 1125 milligrams.

16. A pediatric formula as defined in claim 14 wherein the xanthan gum comprises from about 565 to about 750 milligrams.

17. A pediatric formula as defined in claim 14 wherein the carbohydrate comprises from about 48 to about 59 grams.

18. A pediatric formula as defined in claim 14 wherein the lipid comprises from about 22 to about 28 grams.

19. A pediatric formula as defined in claim 14 wherein the protein comprises from about 11 to about 17 grams.

20. A pediatric formula as defined in claim 14 further comprising vitamins and minerals.

21. A pediatric formula as defined in claim 14 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

22. A pediatric formula as defined in claim 14 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

23. A pediatric formula as defined in claim 14 wherein the protein comprises intact protein selected from the group consisting of soy based protein, milk based protein, casein protein, whey protein, rice protein, beef collagen, pea protein, potato protein, and mixtures thereof.

24. A pediatric formula as defined in claim 14 wherein the protein comprises hydrolyzed protein selected from the group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

25. A pediatric formula as defined in claim 14 wherein the protein comprises free amino acids selected from the group consisting of tryptophan, tyrosine, cystine, taurine, L-methionine, L-arginine, and carnitine, and mixtures thereof.

26. A pediatric formula as defined in claim 14 wherein the carbohydrate is selected from the group consisting of hydrolyzed, intact, natural and chemically modified starches sourced from corm, tapioca, rice or potato in waxy or non waxy forms; sugars such as glucose, fructose, lactose, sucrose, maltose, high fructose corn syrup; and mixtures thereof.

27. A method for providing nutrition to pediatric patients comprising administering an effective amount of a pediatric formula comprising, based on a 100 kcal basis: about 8 to about 16 grams carbohydrate, about 3 to about 6 grams lipid, about 1.8 to about 3.3 grams protein, and a tolerance improver consisting of a single hydrocolloid which is selected from the group consisting of xanthan gum in yhe amounts of about 37 to 370 milligrams. about 370 milligrams-xanthan gum.

28. A method as defined in claim 27 wherein the xanthan gum comprises from about 74 to about 222 milligrams.

29. A method as defined in claim 27 wherein the xanthan gum comprises from about 111 to about 148 milligrams.

30. A method as defined in claim 27 wherein the carbohydrate comprises from about 9.4 to about 12.3 grams.

31. A method as defined in claim 27 wherein the lipid comprises from about 4.7 to about 5.6 grams.

32. A method as defined in claim 27 wherein the protein comprises from about 2.4 to about 3.3 grams.

33. A method as defined in claim 27 further comprising vitamins and minerals.

34. A method as defined in claim 33 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

35. A method as defined in claim 27 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

36. A method as defined in claim 27 wherein the protein comprises intact protein selected from the group consisting of soy based protein, milk based protein, casein protein, whey protein, rice protein, beef collagen, pea protein, potato protein, and mixtures thereof.

37. A method as defined in claim 27 wherein the protein comprises hydrolyzed protein selected from the. group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

38. A method as defined in claim 27 wherein the protein comprises free amino acids selected from the group consisting of tryptophan, tyrosine, cystine, taurine, L-methionine, L-arginine, and carnitine, and mixtures thereof.

39. A method as defined in claim 27 wherein the carbohydrate is selected from the group consisting of hydrolyzed, intact, natural and chemically modified starches sourced from corn, tapioca, rice or potato in waxy or non waxy forms; sugars such as glucose, fructose, lactose, sucrose, maltose, high fructose corn syrup; and mixtures thereof.

40. A method for providing nutrition to pediatric patients comprising administering an effective amount of a pediatric formula reconstituted from a powdered composition which comprises, based on 100 grams of powder, about 30 to about 90 grams carbohydrate, about 15 to about 30 grams fat, about 8 to about 17 grams protein, and a tolerance improver consisting of a single hydrocolloid which is selected from the group consisting of xanthan gum in amounts of about 188 to about 1880 milligrams.

41. A method as defined in claim 40, wherein the xanthan gum comprises from about 375 to about 1125 milligrams.

42. A method as defined in claim 40 wherein the xanthan gum comprises from about 565 to about 750 milligrams.

43. A method as defined in claim 40 wherein the carbohydrate comprises from about 48 to about 59 grams.

44. A method as defined in claim 40 wherein the lipid comprises from about 22 to about 28 grams.

45. A method as defined in claim 40 wherein the protein comprises from about 11 to about 17 grams.

46. A method as defined in claim 40 wherein the formula further comprises vitamins and minerals.

47. A method as defined in claim 46 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

48. A method as defined in claim 40 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

49. A method as defined in claim 40 wherein the protein comprises intact protein selected from the group consisting of soy based protein, milk based protein, casein protein, whey protein, rice protein, beef collagen, pea protein, potato protein, and mixtures thereof.

50. A method as defined in claim 40 wherein the protein comprises hydrolyzed protein selected from the group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

51. A method as defined in claim 40 wherein the protein comprises free amino acids selected from the group consisting of tryptophan, tyrosine, cystine, taurine, L-methionine, L-arginine, and carnitine, and mixtures thereof.

52. A method as defined in claim 40 wherein the carbohydrate is selected from the group consisting of hydrolyzed, intact, natural and chemically modified starches sourced from corm, tapioca, rice or potato in waxy or non waxy forms; and sugars such as glucose, fructose, lactose, sucrose, maltose, high fructose corn syrup; and mixtures thereof.

53. A method for improving tolerance in pediatric patients comprising administering an effective amount of a pediatric formula comprising, based on a 100 kcal basis: about 8 to about 16 grams carbohydrate, about 3 to about 6 grams lipid, about 1.8 to about 3.3 grams protein, and a tolerance improver consisting of a single hydrocolloid which is selected from the group consisting of xanthan gum in the amounts of about 37 to 370 milligrams.

54. A method as defined in claim 53 wherein the xanthan gum comprises from about 74 to about 222 milligrams.

55. A method as defined in claim 53 wherein the xanthan gum comprises from about 111 to about 148 milligrams.

56. A method as defined in claim 53 wherein the carbohydrate comprises from about 9.4 to about 12.3 grams.

57. A method as defined in claim 53 wherein the lipid comprises from about 4.7 to about 5.6 grams.

58. A method as defined in claim 53 wherein the protein comprises from about 2.4 to about 3.3 grams.

59. A method as defined in claim 53 further comprising vitamins and minerals.

60. A method as defined in claim 53 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

61. A method as defined in claim 53 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

62. A method as defined in claim 53 wherein the protein comprises intact protein selected from the group consisting of soy based protein, milk based protein, casein protein, whey protein, rice protein, beef collagen, pea protein, potato protein, and mixtures thereof.

63. A method as defined in claim 53 wherein the protein comprises hydrolyzed protein selected from the group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

64. A method as defined in claim 53 wherein the protein comprises free amino acids selected from the group consisting of tryptophan, tyrosine, cystine, taurine, L-methionine, L-arginine, and 'carnitine, and mixtures thereof.

65. A method as defined in claim 53 wherein the carbohydrate is selected from the group consisting of hydrolyzed, intact, natural and chemically modified starches sourced from corn, tapioca, rice or potato in waxy or non waxy forms; sugars such as glucose, fructose, lactose, sucrose, maltose, high fructose corn syrup; and mixtures thereof.

66. A method of improving tolerance in pediatric patients comprising administering an effective amount of a pediatric formula reconstituted from a powdered composition which comprises, based on 100 grams of powder, about 30 to about 90 grams carbohydrate, about 15 to about 30 grams fat, about 8 to about 17 grams hydrolysate protein, and a tolerance improver consisting of a single hydrocolloid which is selected from the group consisting of xanthan gum in amounts of about 188 to 1880 milligrams.

67. A method as defined in claim 66 wherein the xanthan gum comprises from about 375 to about 1125 milligrams.

68. A method as defined in claim 66 wherein the xanthan gum comprises from about 565 to about 750 milligrams.

69. A method as defined in claim 66 wherein the carbohydrate comprises from about 48 to about 59 grams.

70. As A method as defined in claim 66 wherein the lipid comprises from about 22 to about 28 grams.

71. A method as defined in claim 66 wherein the protein comprises from about 11 to about 17 grams.

72. A method as defined in claim 66 wherein the formula further comprises vitamins and minerals.

73. A method as defined in claim 72 wherein the vitamins and minerals are selected from the group consisting of calcium, phosphorus, sodium, chloride, magnesium, manganese, iron, copper, zinc, selenium, iodine, Vitamins A, E, C, D, K and the B complex, and mixtures thereof.

74. A method as defined in claim 66 wherein the lipid is selected from the group consisting of coconut oil, soy oil, corn oil, olive oil, safflower oil, high oleic safflower oil, MCT oil (medium chain triglycerides), sunflower oil, high oleic sunflower oil, palm oil, palm olein, canola oil, lipid sources of arachidonic acid and docosahexaneoic acid, and mixtures thereof.

75. A method as defined in claim 66 wherein the protein comprises intact protein selected from the group consisting of soy based protein, milk based protein, casein protein, whey protein, rice protein, beef collagen, pea protein, potato protein, and mixtures thereof.

76. A method as defined in claim 66 wherein the protein comprises hydrolyzed protein selected from the group consisting of soy protein hydrolysate, casein protein hydrolysate, whey protein hydrolysate, rice protein hydrolysate, potato protein hydrolysate, fish protein hydrolysate, egg albumen hydrolysate, gelatin protein hydrolysate, a combination of animal and vegetable protein hydrolysates, and mixtures thereof.

77. A method as defined in claim 66 wherein the protein comprises free amino acids selected from the group consisting of tryptophan, tyrosine, cystine, taurine, L-methionine, L-arginine, and carnitine, and mixtures thereof.

78. A method as defined in claim 66 wherein the carbohydrate is selected from the group consisting of hydrolyzed, intact, natural and chemically modified starches sourced from corn, tapioca, rice or potato in waxy or non waxy forms; and sugars such as glucose, fructose, lactose, sucrose, maltose, high fructose corn syrup; and mixtures thereof.

\* \* \* \* \*

UNITED STATES PATENT AND TRADEMARK OFFICE
CERTIFICATE OF CORRECTION

PATENT NO. : 6,365,218 B1
DATED : April 2, 2002
INVENTOR(S) : Borschel et al.

It is certified that error appears in the above-identified patent and that said Letters Patent is hereby corrected as shown below:

Column 14,
Line 12, delete "15".

Column 15,
Line 38, change "corm" to -- corn --.
Line 48, change "yhe" to -- the --.
Lines 49-50, delete "about 370 milligrams-xanthan gum."

Column 17,
Line 18, change "corm" to -- corn --.

Column 18,
Line 2, delete " ' ".
Line 18, insert -- about -- before "1880 milligrams."
Line 25, delete "As".

Signed and Sealed this

Seventeenth Day of September, 2002

Attest:

Attesting Officer

JAMES E. ROGAN
*Director of the United States Patent and Trademark Office*